US005778724A

United States Patent [19]
Clapp et al.

[11] Patent Number: 5,778,724
[45] Date of Patent: Jul. 14, 1998

[54] METHOD AND DEVICE FOR MONITORING WEB BAGGINESS

[76] Inventors: Todd E. Clapp; John J. Costello, both of P.O. Box 33427, St. Paul, Minn. 55133-3427

[21] Appl. No.: 524,088

[22] Filed: Sep. 7, 1995

[51] Int. Cl.$^6$ .............................. G01L 5/04; G01N 21/84
[52] U.S. Cl. .................. 73/159; 250/559.01; 356/431
[58] Field of Search ............ 75/159; 250/559.01, 250/559.12, 559.13, 559.2, 559.24, 559.29, 559.39, 559.41, 559.42, 559.48, 559.49; 356/238, 429, 430, 431

[56] References Cited

U.S. PATENT DOCUMENTS

| | | | |
|---|---|---|---|
| 3,385,106 | 5/1968 | Fargo et al. | 73/159 |
| 3,612,700 | 10/1971 | Nelson | 356/153 |
| 3,892,492 | 7/1975 | Eichenberger | 356/429 X |
| 3,930,167 | 12/1975 | Hsiao | 250/572 |
| 3,979,935 | 9/1976 | Edwards et al. | 73/159 X |
| 4,004,153 | 1/1977 | Obser et al. | 250/559.49 |
| 4,591,726 | 5/1986 | Schenk | 356/431 X |
| 4,610,739 | 9/1986 | Jensen | 156/64 |
| 4,619,527 | 10/1986 | Leuenberger et al. | 356/238 |
| 4,760,271 | 7/1988 | Brenholdt | 356/430 X |
| 4,792,698 | 12/1988 | Pryor | 250/561 |
| 4,936,141 | 6/1990 | Anderson, Jr. et al. | 73/159 |
| 4,966,455 | 10/1990 | Avni et al. | 250/559.01 X |
| 5,025,665 | 6/1991 | Keyes, IV et al. | 73/159 |
| 5,047,640 | 9/1991 | Bruchhschweiler et al. | 356/431 X |
| 5,130,559 | 7/1992 | Leifeld et al. | 250/559.41 X |
| 5,182,722 | 1/1993 | Hain | 73/159 X |
| 5,317,913 | 6/1994 | Feistkorn et al. | 73/159 |
| 5,365,074 | 11/1994 | Genovese | 250/559.29 |
| 5,378,918 | 1/1995 | Ottl | 250/559.01 |

FOREIGN PATENT DOCUMENTS

| | | | |
|---|---|---|---|
| 0 104 811 | 4/1984 | European Pat. Off. | B29C 59/04 |
| 56-72308 | 6/1981 | Japan . | |
| WO 92/10419 | 6/1992 | WIPO | B65H 23/192 |
| WO 94/15173 | 7/1994 | WIPO | G01B 11/24 |

*Primary Examiner*—George M. Dombroske
*Assistant Examiner*—Paul D. Amrozowicz
*Attorney, Agent, or Firm*—Michaele A. Hakamaki

[57] ABSTRACT

A method of monitoring bagginess of a web transverse to a longitudinal direction of the web is disclosed. The method includes projecting a first reference light onto a front face of the web transverse to the web, and projecting a first measurement light onto the front face of the web non-perpendicular to the front face and transverse to the web. The longitudinal distance on the front face of the web between a point along the first reference light and a corresponding point along the first measurement light are compared to determine bagginess of the web. A method of monitoring bagginess of a web in the longitudinal direction of the web is also disclosed.

21 Claims, 3 Drawing Sheets

METHOD AND DEVICE FOR MONITORING WEB BAGGINESS

TECHNICAL FIELD

The present invention relates to a method for monitoring the bagginess of web materials. More particularly, the present invention relates to a method for monitoring the bagginess of a web in both the crossweb and machine directions.

BACKGROUND OF THE INVENTION

Paper materials, plastic film materials, and other materials commonly provided in sheet and strip form are often initially produced as continuous lengths of material, usually referred to as "webs," which are wound onto cores. A web will typically be subjected to several processing steps before a final product is produced, including coating steps, converting steps, and the like. In these processing steps, the web will generally be unwound from a core and pass over a number of roller type devices where the web can be stretched under tension, subjected to temperature changes, or both, to try to achieve certain web characteristics. However, these temperature and tension variations can cause the web to stretch or shrink unevenly across the crossweb direction and in the machine direction of the web. When the web returns to its steady-state condition, the stretched or shrunk areas will often become baggy, which can develop into creases or wrinkles in the web. These changes in the condition of the web can cause problems in later web handling operations, including winding and converting. For example, it is more difficult to properly slit a creased or wrinkled web into strips than to slit a web without bagginess problems into strips. However, if the bagginess of a web can be monitored while the web is running through a manufacturing process such as a coating or a slitting process, it is often possible to control or eliminate the web bagginess by changing the tension on the web or by adjusting some other processing parameter.

In some cases, the crossweb bagginess in the web may be so great that it cannot be corrected by adjusting the processing conditions. In these cases, the processing operation can be stopped and the portion of the web having excessive bagginess can be removed from the manufacturing sequence by cutting out the material that is excessively baggy. This removed portion of the web can then be reworked by another process to correct the bagginess problem or can be discarded or recycled if the bagginess cannot be corrected. To minimize waste, it is therefore beneficial for operators of manufacturing equipment to use on-line monitoring methods during web processing or handling to detect when a web has an unacceptable level of bagginess. This information can provide substantial cost savings for the manufacturer because it can eliminate the cost of continuing to process a defective web. In other words, it is less expensive for a manufacturer to discard or recycle a defective web early in the processing of a web product, when it has only been run through one or two processing steps, than it is to discard the web product later in the process, after it has been run through several additional processing steps.

Web bagginess is particularly a problem in the crossweb or transverse direction, which is the direction that is transverse to the longitudinal or machine direction of the web as it is running through a manufacturing process. There are methods available for monitoring bagginess, which include contact and non-contact methods, as further discussed below.

Contact methods of monitoring the bagginess of a web typically use a device that physically contacts the surface of the web. One method of measuring web bagginess is to stop the web handling process and use a yard stick or tape measure to measure the approximate width of the web at a particular location. This width measurement is compared to the expected width of the web; if the actual measured width is wider than the expected width, it is likely that the web has stretched and appropriate process adjustments can be made to compensate for web bagginess. This method is most often used for checking a web at discrete points and is not effective as an on-line method for constant monitoring of a web or for detecting sudden changes in web bagginess because the method is not used when the web process is running.

Another example of a contact method of monitoring web bagginess is described in U.S. Pat. No. 5,317,913 (Feistkorn et al.). Feistkorn et al. describes a web sensing roller that contacts the surface of a web, where a carrier of the web sensing roller is guided within a housing to be movable in a direction perpendicular to the plane of the web. The web sensing roller presses against the surface of the web as the web moves past the web sensing roller, and an apparatus measures the distance that the web sensing roller moves from a predetermined reference position, which corresponds to the bagginess in the web.

In some cases, a web may be particularly susceptible to damage by devices physically contacting the web surface during processing. For these webs, it is undesirable for monitoring devices to contact the web during web processing. Known non-contact methods to monitor the bagginess of a web use a single light in combination with a camera and a computer system. In this method, a single line of light is projected orthogonally to illuminate the object of interest, such as a web, and the image of this line is captured with a camera directed at 45° to the plane of the web. Alternatively, a single line of light is projected at 45° to the web surface and the image of this line is captured with a camera directed orthogonally to the web. In either method, the captured image is transferred to a computer system that analyzes the image, which can send a signal that corresponds to the level of web bagginess measured. Based on this signal, appropriate adjustments to the manufacturing process may then be made to compensate for any bagginess in the web.

SUMMARY OF THE INVENTION

The method of monitoring bagginess of a web transverse to a longitudinal direction of the web comprises the steps of projecting a first reference light from a first light source onto a front face of the web transverse to the web, and projecting a first measurement light from a second light source onto the front face of the web non-perpendicular to the front face and transverse to the web. The longitudinal distance on the front face of the web between a point along the first reference light and a corresponding point along the first measurement light are compared to determine bagginess of the web.

Additionally, the method can include the steps of recording the position of the first reference light and recording the position of the first measurement light, providing those recorded positions to a computer which measures the distance between them, and sending a signal from the computer to an external source. The external source can then make adjustments to correct any bagginess in the web.

The method can also include projecting more than one reference light onto the front face of the web from a third light source and can include monitoring bagginess of a web in the longitudinal direction of the web.

DETAILED DESCRIPTION

The invention is a method and an apparatus for monitoring the amount of bagginess in a web product during the processing of the web. The term "baggy" describes the condition of areas of a web product, such as a film, that have become stretched or relaxed during processing. When a web is positioned between guide rollers or the like, any baggy areas in the web typically will hang down from the position of a "flat" web, which has no baggy areas.

More specifically, the method is appropriate for on-line monitoring of the bagginess as the web moves in a manufacturing process along a predetermined path. When used in an on-line monitoring situation, the method can help detect sudden changes in web bagginess and can help monitor the steady state condition of bagginess in the web. The method and apparatus can also be used to record the amount of bagginess in the web at specific locations and times.

Figure 1:
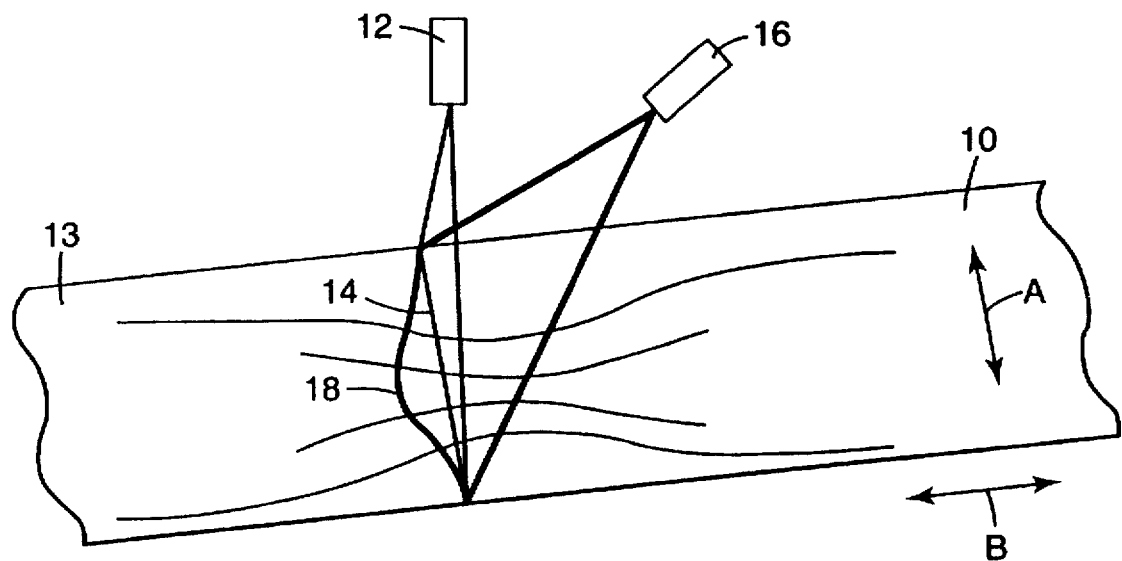
FIG. 1 is a schematic view of a system for monitoring web bagginess in accordance with the present invention.
Figure 2:
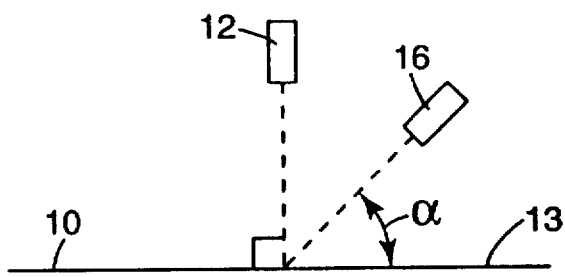
FIG. 2 is a schematic view of the system of FIG. 1 viewed from the side with a flat web.
Figure 3:
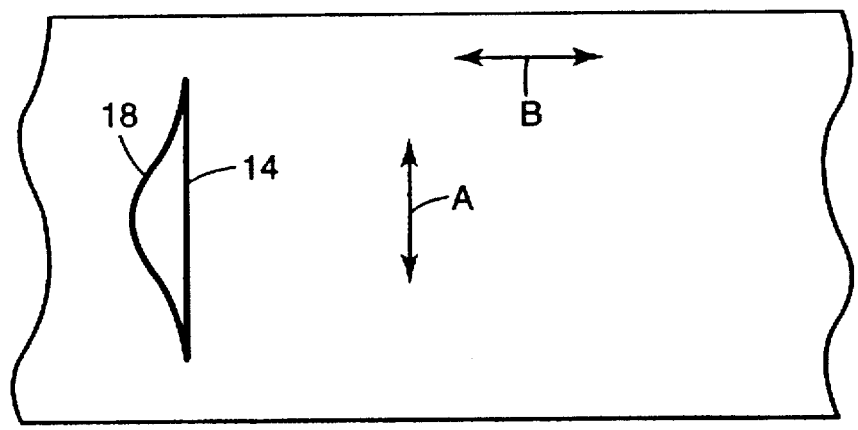
FIG. 3 is a schematic view from above the web of an area of bagginess of the web of FIG. 1.

FIGS. 1, 2, and 3 illustrate one embodiment of the invention for measuring the bagginess of a web 10 in a crossweb direction of the web. The crossweb direction is shown as the direction A in FIGS. 1 and 3, and the opposite direction is commonly referred to as the machine direction, shown as the direction B in FIGS. 1, 3, and 4.

To measure the bagginess of the web 10 in the transverse direction, a first light source 12 is positioned above a front face 13 of the web 10. The web 10 is illustrated as it would be in any unsupported web handling situation, such as between guide rollers. The light source 12 is preferably a laser line generator that can generate a laser line that is visible to the human eye. Examples include single line laser projectors commercially available from Lasiris, Inc., St. Lawrence, Quebec, Canada. Alternatively, the light source 12 can be a solid state laser directed at a galvanometer to generate a laser line, or can be some other type of light source that can be directed at a surface of the web 10 to produce light on that surface. As shown, the light source 12 generates a reference line 14 which is projected perpendicularly onto the front face 13 of the web 10. Because the view in FIG. 1 shows the web 10 from a location spaced from the light source 12 in the machine direction, the reference line 14 does not appear perpendicular. Although the reference line 14 can extend across the entire width of the web 10, the laser line 14 can extend across only one or more portions of the web 10. For example, if web bagginess is only a concern in one portion of the width of the web 10, the laser line 14 can extend only across that portion. Similarly, the light can also be a point source or series of point sources.

A second light source 16 is generally positioned above the front face 13 of the web 10 to project a laser line at an angle with the web 10 that differs from the angle that the laser line 14 projected from the light source 12 makes with the web 10. The light source 16 is also preferably a laser generator that is capable of generating a laser line that is visible to the human eye, but can be some other type of light source that produces a line of light that can be projected onto a surface. The light source 16 can be the same type as the light source 12 or can be a different type. The light source 16 generates a measurement line 18 which is projected onto the front face 13 of the web 10. As with the reference line 14, the measurement line 18 can also extend across the entire width of the web 10 or across only a particular portion of the web 10. In any case, the method of this invention can be used to measure the bagginess of the web 10 in those portions of the web 10 having both a reference line 14 and a measurement line 18 projected onto its front face 13.

One method is shown in FIG. 2, where the light source 12 projects a line 14 perpendicular to the front face 13 of the web 10 and the light source 16 projects a line 18 from an angle $\alpha$ of 45° to the front face 13. The light sources 12, 16 can be located anywhere in the transverse direction above the web 10, so long as the light sources 12, 16 can project light onto the area of the web 10 that is to be monitored. As shown, the light sources 12, 16 are positioned so that the measurement line 18 from the light source 16 and the reference line 14 from the light source 12 intersect at or near the front face 13 of the web 10 when the web 10 is flat. When the lines 14 and 18 intersect or coincide in this manner, only a single line is visible to the human eye when viewed from above the web 10. In this situation, there is no web bagginess (the web 10 is flat).

However, when there is bagginess in the web 10 the reference line 14 will remain straight in the transverse direction and the measurement line 18 will appear deformed in the machine direction to project an image that corresponds with the topography of the baggy surface of the web 10. FIG. 3 shows the position of the lines 14 and 18 on the baggy portion of the web 10 of FIG. 1 when viewed from a point above and perpendicular to the web 10. As shown, the reference line 14 is straight in the transverse direction and the measurement line 18 is deformed in the machine direction from the reference line 14 in the baggy area of the web 10.

Although bagginess is often referred to as web deformation below the plane of a flat web 10, it is also possible for "rises" or localized web displacement to occur above the plane of a flat web 10. The invention can be used to measure both types of web displacement. For example, when FIG. 3 illustrates the deformation of the web 10 below the plane of a flat web 10, deformation of the web 10 above the plane of a flat web would cause the measurement line to project on the opposite side of the reference line 14 in the machine direction. In fact, FIG. 3 may be an illustration of web deformation either above or below the plane of a flat web 10, depending on where the light sources 12 and 16 are positioned relative to each other.

The light source 12 need not project a reference line 14 perpendicular to the web 10. Rather, the light source 12 can project a reference line 14 at any angle that is different from the angle which the light source 16 projects the measurement line 18 onto the web 10 onto the front face 13 of the web 10. Both the reference line 14 and the measurement line 18 will be straight in the transverse direction when the web 10 is flat. When the web 10 is baggy, neither of the lines 14, 18 will be straight, but the lines 14, 18 will still be spaced from each other.

Figure 4:
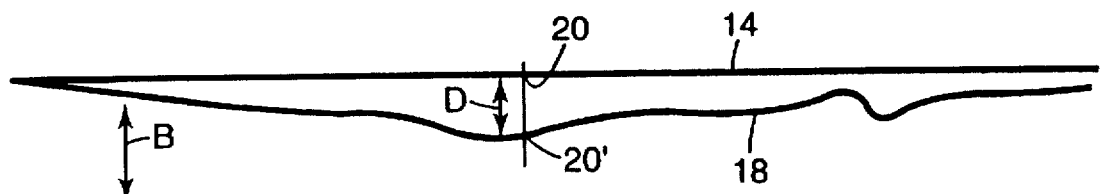
FIG. 4 is a schematic view of a reference line and a measurement line as projected onto the face of a baggy web.

FIG. 4 illustrates another example viewed from above a baggy web 10 of a reference line 14 and a measurement line 18 projected onto the web 10. Specifically, the distance D in the machine direction of FIG. 4 corresponds to the distance between a point 20 on the reference line 14 and a point 20' on the measurement line 18. When the web 10 is flat and only one line is visible, the points 20 and 20' would overlap each other on the web 10. However, when the web 10 is baggy as shown in FIG. 4, the point 20' moves to a position spaced by a distance D from the point 20 to correspond to the amount of bagginess in the web 10.

Figure 5:
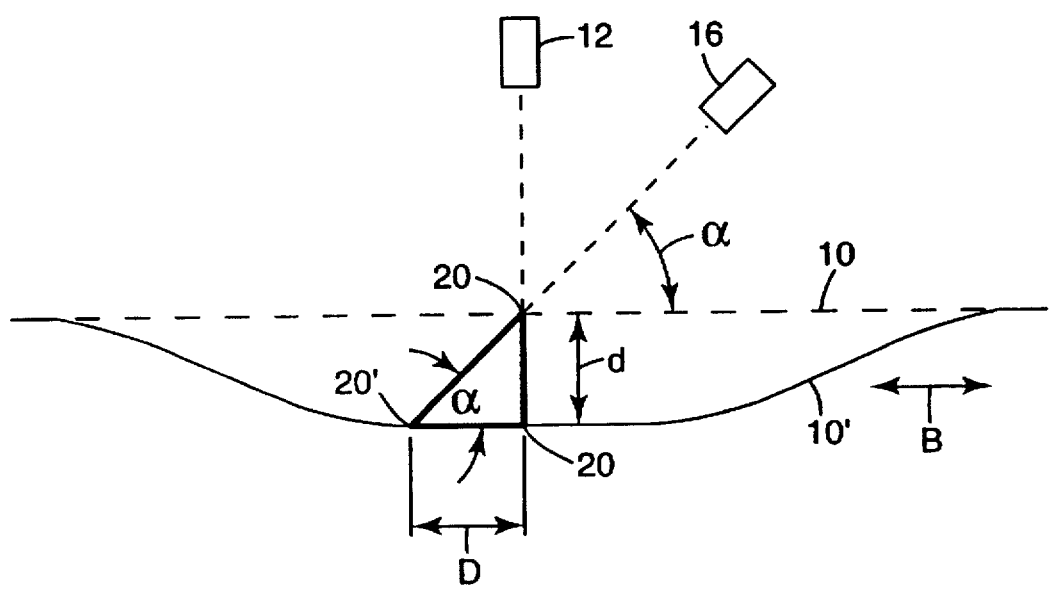
FIG. 5 is a schematic view of the system of FIG. 1 viewed from the side with a baggy web.

As illustrated in FIG. 5, the relationship between the distance D and an amplitude d of the bagginess of the web 10 is determined by the angle $\alpha$ at which the measurement line 18 is projected onto the front face 13 of the web 10. More specifically, FIG. 5 shows the plane of a flat web 10 as a dashed line on which the lines 14 and 18 projected from light sources 12 and 16 coincide or intersect at point 20. A baggy portion of the web 10 is shown with a solid line as a web 10'. As shown, a triangle is created by the point 20 on the flat web 10, the point 20 on the baggy web 10', and the point 20' on the baggy web 10'. When the angle $\alpha$ is 45°, the distance between a point 20 on the reference line 14 and a point 20' on the measurement line 18 is the same as the amplitude d that the web 10' has deviated from the flat plane of the web 10. An increase in the amplitude d, which occurs when the web bagginess increases, therefore corresponds to an equal increase in the distance D between a point on the reference line 14 and a point on the measurement line 18. Similarly, when the web bagginess decreases by an amount equal to the amplitude d, the distance D between a point on the reference line 14 and a point on the reference line 18 decreases by a corresponding amount.

The light source 16 can also be positioned to project a measurement line 18 from an angle $\alpha$ other than 45° as previously described. If the angle $\alpha$ is projected is greater than 45°, any bagginess in the web 10 will again cause the measurement line 18 to vary from the straight line that would be projected if there were no bagginess in the web 10. However, the distance D will be smaller than the amplitude d that a baggy web 10' has actually deviated from the plane of a flat web 10. Conversely, if the angle $\alpha$ from which the measurement line 18 is projected onto the web 10 is less than 45° to the front face 13 of the web 10, the distance D will be larger than the amplitude d that the baggy web 10' has actually deviated from the plane of a flat web 10.

In another method, the reference line 14 can be offset from the measurement line 18 so that the lines 14 and 18 are parallel to and spaced from each other and the points 20 and 20' are spaced from each other even when the web 10 is flat. The reference line 14 can be positioned on either side of the measurement line 18 in the machine direction. The points 20 and 20' are spaced differently with respect to the other where the web 10 is baggy. Variations in the bagginess of the web 10 will change the distance between points 20 and 20' by an amount that is proportional to the amount of web bagginess, depending on the angle $\alpha$ as described above. Varying the angle $\alpha$ changes the relationship of the distance between points on the lines 14 and 18 and the actual amplitude of the bagginess of the web 10 may be changed.

Figure 6:
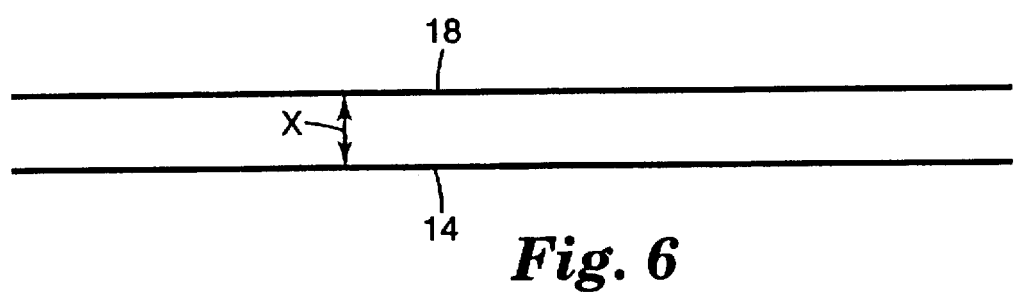
FIG. 6 is a schematic view of a reference line and a measurement line as projected onto a flat web and separated by a specific distance.
Figure 7:
FIG. 7 is a schematic view of the reference line and measurement line of FIG. 6 as projected onto a baggy web.

FIGS. 6 and 7 show this method where the distance between lines 14 and 18 is fixed as X when the web is flat. As shown in FIG. 6, when the web 10 is flat, the reference line 14 is projected orthogonally onto the web 10 and the measurement line 18 is projected from an angle $\alpha$ onto the web 10 so that the lines 14 and 18 are separated by a predetermined constant distance X. The distance X represents the maximum acceptable bagginess of a web 10. In operation, any deviation of the measurement line 18 indicates bagginess. When the measurement line 18 crosses the reference line 14 on a baggy web 10, as shown in FIG. 7, the web 10 has exceeded its predetermined acceptable level of bagginess.

When projecting the lines 14 and 18 so that they are separated by some distance on the front face 13 of the web 10, the light sources 12 and 16 can be positioned so that the projected lines 14 and 18 do not cross each other. Alternatively, the light sources 12 and 16 can be positioned so that the projected lines 14 and 18 cross each other at some point above the web 10 and are separated from each other when they reach the front face 13 of the web 10.

Figure 8:
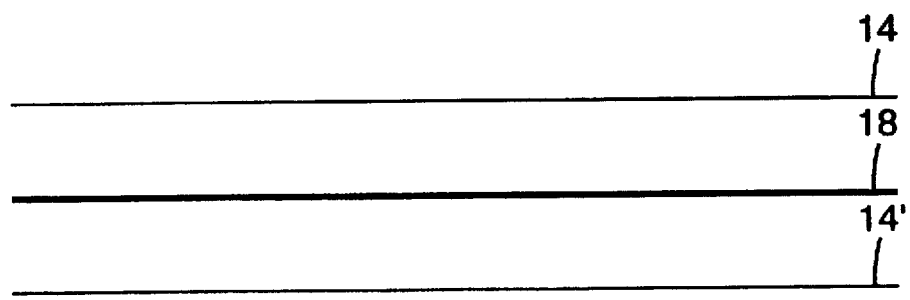
FIG. 8 is a schematic view of two reference lines and one measurement line as projected onto a flat web.
Figure 9:
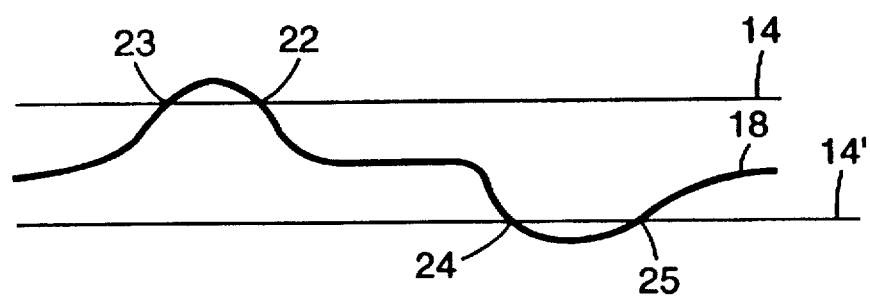
FIG. 9 is a schematic view of the two reference lines and one measurement line of FIG. 8 as projected onto a baggy web.

The present invention can also be used with more than one reference line to more specifically determine specific web bagginess characteristics. FIGS. 8 and 9 illustrate the use of two reference lines 14 and 14' with a single measurement line 18. Reference lines 14 and 14' can be positioned so that an operator can determine the relative displacement of a web 10 by comparing the distance between the measurement line 18 and the reference line 14' to the distance between the measurement line 18 and the reference line 14.

The two reference lines 14 and 14' can also be used to simultaneously determine whether the web 10 exceeds limits of web deformation both above and below the plane of a flat web 10. For example, FIG. 9 illustrates a situation where the web 10 exceeds both limits of web deformation, where lines 14 and 14' are positioned to be the limits of web deformation. Specifically, measurement line 18 crosses reference line 14 at points 22 and 23, which could represent the limit of web deformation above or below the plane of a flat web 10. Similarly, measurement line 18 crosses reference line 14' at points 24 and 25, which could represent the web deformation either below or above the plane of a flat web 10, but in the opposite direction (i.e., above or below the plane of a flat web 10) of the deformation at points 22 and 23. The two reference lines 14 and 14' could also be positioned on the same side of the measurement line 18 at distances that could represent two different limits of web deformation above or below the plane of a flat web 10.

The method described above can also be used to measure the bagginess of the web 10 in the machine direction by projecting at least one reference line 14 and at least one measurement line 18 in the machine direction of the web rather than in the transverse direction. Any of the described methods for measuring bagginess in the transverse direction can be used for bagginess measurements in the machine direction. The method can also be used to measure bagginess in other desired directions besides the transverse direction and the machine direction as long as both a reference line 14 and a measurement line 18 are projected onto the web 10 in the desired direction.

Moreover, the present invention can be used to simultaneously measure the bagginess of the web 10 in both the machine direction and the transverse direction by projecting at least one reference line and at least one measurement line in the transverse direction and projecting at least one reference line and at least one measurement line in the machine direction. Each of the respective sets of reference lines and measurement lines can then be independently considered for bagginess in the crossweb and longitudinal directions.

A viewer's perception of the distance D on the front face 13 of a web 10 can vary depending on the angle and position from which the web 10 is viewed relative to the reference line 14 and the measurement line 18. For example, if an operator is looking in a perpendicular direction from a point very near the light source 12 at the web 10, the operator will perceive the lines 14 and 18 and any distances D between points on the lines 14 and 18 as they actually appear on the web 10. However, if the operator is looking at the web 10 from a point at some distance in the machine direction from the light source 12, the operator's view of the lines 14 and 18 and any distances D will be different than the distances D when viewed perpendicular to the web 10. Therefore, in those cases where the distance D is important for determining the amplitude d of web bagginess, it is most accurate to view the web 10 from a point above and perpendicular to the web 10, as close to the light source 12 as possible. However, in those cases where viewer is looking for the crossing of a measurement line 18 and a reference line 14, the viewer can view the web from any angle above the web as long as the viewer can see both lines.

These systems can be used through visual inspection of variations in the measurement line 18 with respect to the reference line 14 during a web handling operation. A system incorporating cameras, computers, or other visualization equipment can also be used to monitor the position and changes in the measurement line 18 with respect to the reference line 14. For instance, a camera can be positioned above the web 10 to monitor changes in the measurement line 18 and these changes can be provided as input to a computer system. The computer system can then calculate web bagginess based on the input provided. The web bagginess calculated can then simply be recorded in a database or can be used as input to allow web handling equipment to be adjusted to correct web bagginess problems.

We claim:

1. A method of monitoring bagginess of a web transverse to a longitudinal direction of the web, comprising the steps of:

projecting a first reference light at a first angle from a first light source onto a front face of the web transverse to the web;

projecting a first measurement light at a second angle from a second light source onto the front face of the web non-perpendicular to the front face and transverse to the web, wherein the first angle is different from the second angle; and comparing a longitudinal distance on the front face of the web between a point along the first reference light and a corresponding point along the first measurement light to determine bagginess.

2. The method of claim 1, wherein the step of projecting the first measurement light comprises projecting the first measurement light coincident with the first reference light on the front face of the web when the web is flat.

3. The method of claim 1, wherein the step of projecting the first reference light comprises projecting the first reference light perpendicular to the front face so that the first reference light is straight even when the web is baggy.

4. The method of claim 1, wherein the projecting the first reference light step comprises projecting a first laser beam and the projecting the first measurement light step comprises projecting a second laser beam.

5. The method of claim 4, wherein the first laser beam is a first laser line and the second laser beam is a second laser line.

6. The method of claim 1, further comprising the steps of:

recording a position of the first reference light;

recording a position of the first measurement light;

providing the recorded position of the first reference light and the recorded position of the first measurement light to a computer which measures the distance between the recorded position of the first reference light and the recorded position of the first measurement light;

sending a signal from the computer to an external source; and making adjustments to correct bagginess in the web using the external source.

7. The method of claim 3, wherein the step of projecting a first measurement light onto the front face of the web comprises projecting the first measurement light onto the web at a 45° angle to the front face of the web.

8. The method of claim 7, wherein the steps of projecting the first reference light and projecting the first measurement light comprise projecting the first reference light and the first measurement light such that the first reference light and the first measurement light are coincident on the front face of the web when the web is flat.

9. The method of claim 1, wherein the steps of projecting the first reference light and projecting the first measurement light comprise projecting the first reference light and the first measurement light such that the first reference light is spaced from the first measurement light on the front face of the web when the web is flat.

10. The method of claim 9, wherein the distance between the first reference light and the first measurement light corresponds to a level of bagginess in the web.

11. The method of claim 1, further comprising projecting a second reference light from a third light source onto the front face of the web transverse to the web.

12. An apparatus for monitoring bagginess of a web, comprising:

a first light source which projects a first reference light onto the front face of the web in a direction that is perpendicular to the front face of the web and is one of generally transverse and generally longitudinal to the web; and a second light source which projects a first measurement light onto the front face of the web in a non-perpendicular direction to the front face of the web and generally parallel to the first reference light so that any perpendicular distance between a point along the first reference light and a point along the first measurement light can be viewed to determine web bagginess.

13. A method of monitoring bagginess of a web in a longitudinal direction of the web, comprising the steps of:

projecting a first reference light at a first angle from a first light source onto a front face of the web longitudinal to the web;

projecting a first measurement light at a second angle from a second light source onto the front face of the web non-perpendicular to the front face and longitudinal to the web, wherein the first angle is different from the second angle; and comparing a transverse distance on the front face of the web between a point along the first reference light and a corresponding point along the first measurement light to determine bagginess.

14. The method of claim 13, wherein the step of projecting the first measurement light comprises projecting the first measurement light coincident with the first reference light on the front face of the web when the web is flat.

15. The method of claim 13, wherein the step of projecting the first reference light comprises projecting the first reference light perpendicular to the front face so that the first reference light is straight even when the web is baggy.

16. The method of claim 13, wherein the projecting the first reference light and the projecting the first measurement light steps comprise projecting laser beams.

17. The method of claim 13, further comprising the steps of:
 recording the position of the first reference light;
 recording the position of the first measurement light;
 providing the recorded position of the first reference light and the recorded position of the first measurement light to a computer which measures the distance between the recorded position of the first reference light and the recorded position of the first measurement light;
 sending a signal from the computer to an external source; and
 making adjustments to correct bagginess in the web using the external source.

18. The method of claim 13, wherein the step of projecting a first measurement light onto the front face of the web comprises projecting the first measurement light onto the web at a 45° angle to the front face of the web.

19. The method of claim 18, wherein the steps of projecting the first reference light and projecting the first measurement light comprise projecting the first reference light and the first measurement light such that the first reference light and the first measurement light are coincident on the front face of the web when the web is flat.

20. The method of claim 13, wherein the steps of projecting the first reference light and projecting the first measurement light comprise projecting the first reference light and the first measurement light such that the first reference light is spaced from the first measurement light on the front face of the web when the web is flat.

21. The method of claim 13, further comprising projecting a second reference light from a third light source onto the front face of the web transverse to the web.

* * * * *

UNITED STATES PATENT AND TRADEMARK OFFICE
CERTIFICATE OF CORRECTION

PATENT NO. : 5,778,724
DATED : July 14, 1998
INVENTOR(S) : Todd E. Clapp and John J. Costello It is certified that error appears in the above-identified patent and that said Letters Patent is hereby corrected as shown below:

On Title Page, between [76] Inventors and [21] Appl. No., please insert:
--[73] Assignee: Minnesota Mining and Manufacturing Company, St. Paul, Minn.--

Signed and Sealed this

Twenty-seventh Day of July, 1999

Attest:

Q. TODD DICKINSON

*Attesting Officer*     *Acting Commissioner of Patents and Trademarks*